United States Patent [19]
Grizzaffi

[11] Patent Number: 5,275,592
[45] Date of Patent: Jan. 4, 1994

[54] APPARATUS FOR INCONTINENT MALES

[75] Inventor: Eugenia Grizzaffi, Morgan City, La.

[73] Assignee: Rodney A. Appell, Gretna, La. ; a part interest

[21] Appl. No.: 894,098

[22] Filed: Jun. 5, 1992

[51] Int. Cl.$^5$ .................. A61F 13/72; A61F 13/74
[52] U.S. Cl. .................. 604/396; 604/397; 604/402; 602/72; 2/403
[58] Field of Search .................. 604/393-397, 401, 402, 353, 368; 602/70, 72, 73; 2/403, 402, 405

[56] References Cited

U.S. PATENT DOCUMENTS

| | | | |
|---|---|---|---|
| 741,173 | 10/1903 | Seidel . | |
| 2,024,341 | 12/1935 | DeGraff | 604/353 |
| 2,699,782 | 1/1955 | Chester | 604/353 |
| 2,864,369 | 12/1958 | Morrow | 604/353 |
| 3,035,579 | 5/1962 | Benovic | 604/353 |
| 3,207,155 | 9/1965 | Casey | 2/403 X |
| 3,212,500 | 10/1965 | Bardy | 604/397 X |
| 3,517,666 | 6/1970 | Atlee | 2/403 X |
| 3,616,798 | 11/1971 | Garfinkel . | |
| 3,707,969 | 1/1973 | Sanford . | |
| 4,601,716 | 7/1986 | Smith . | |
| 4,681,577 | 7/1987 | Stern et al. | 604/389 X |
| 4,702,239 | 10/1987 | Ichikawa | 2/403 X |
| 4,710,188 | 12/1987 | Runeman . | |
| 4,731,070 | 3/1988 | Koci . | |
| 4,828,555 | 5/1989 | Hermansson . | |
| 4,901,375 | 2/1990 | Dahlgren . | |
| 4,923,454 | 5/1990 | Seymour et al. | 604/368 |
| 5,012,802 | 5/1991 | Bischoff | 602/73 |
| 5,087,506 | 2/1992 | Palumbo | 604/368 X |
| 5,094,234 | 3/1992 | Searcy | 602/73 X |

*Primary Examiner*—Randall L. Green
*Assistant Examiner*—Mary Beth Jones
*Attorney, Agent, or Firm*—Pravel, Hewitt, Kimball & Krieger

[57] ABSTRACT

A device for incontinent males includes an athletic supporter having a pocket and a disposable insert which fits into the pocket. The athletic supporter includes a waist band which fits around the waist of a user of the device and which helps to hold the pocket adjacent the penis of the user. The disposable insert which is placed in the pocket of the athletic supporter is substantially cylindrical and sized to be received in the pocket of the athletic supporter includes a layer of absorbent material, a waterproof material on the exterior of the layer of absorbent material, and a cavity sized to receive a human penis. The layer of absorbent material preferably includes a first portion which surrounds the cavity and a second portion which extends between the cavity and the second, closed end of the insert, the second portion having a length of between one half and three quarters of the distance between the first, open end of the insert and the second, closed end of the insert. The insert preferably also includes an inner liner which separates the user's penis from the layer of absorbent material so that moisture in the absorbent layer does not come into contact with the user's skin.

17 Claims, 2 Drawing Sheets the 
APPARATUS FOR INCONTINENT MALES

BACKGROUND OF THE INVENTION

1. Field of the Invention

The present invention relates to devices for incontinent males, and more particularly to apparatus for trapping urine leaking from the penis of an incontinent male.

2. General Background of the Invention

There are a number of products which have been patented which attempt to help incontinent males.

Seidel, U.S. Pat. No. 741,173, discloses a "Sanitary Urinal" which includes a water-tight, open-top bag preferably made of thin sheet-rubber. Inside the bag is a sponge to absorb urine. The bag is attached to a belt and encloses the penis and scrotum of the user.

De Graff, U.S. Pat. No. 2,024,341, discloses a "Urinary Receptacle" which includes a similar bag attached to a belt. It includes a removable absorbent insert and has a hole through which the user inserts his penis.

Chester, U.S. Pat. No. 2,699,782, discloses a "Bed-Type Urinal" which includes a bag similar to that of Seidel and which is also attached to a belt. It also includes a removable, absorbent insert.

Morrow, U.S. Pat. No. 2,864,369, discloses a "Urine Bag" which includes a bag similar to that of Seidel and which is also attached to a belt. It also includes a removable, absorbent insert.

Benovic, U.S. Pat. No. 3,035,579, discloses a "Urine Retaining Device" which includes a bag having inner and outer waterproof liners with a removable absorbent insert which fits in-between the liners.

Garfinkel, U.S. Pat. No. 3,616,798, discloses a "Dry Incontinent Garment" which includes an outer, waterproof layer, an inner, fluid-permeable layer, and an absorbent layer in-between the inner and outer layers. The multilayered device is held on a person using a belt.

Sanford, U.S. Pat. No. 3,707,969, discloses an "Incontinence Device" which is similar to a diaper.

Smith, U.S. Pat. No. 4,601,716, discloses a "Disposable Sanitary Sheath for Males" which includes a bag having an outer waterproof liner, an inner, moisturepermeable liner, and an absorbent pad in-between the liners. Elastic or hook-and-loop fastening material hold the bag on the end of a human penis.

Runeman, U.S. Pat. No. 4,710,188, entitled "Incontinence Protector and a Method for its Manufacture," discloses a bag having an outer waterproof liner and an inner absorbent pad. It apparently receive the penis and scrotum of a user.

Koci, U.S. Pat. No. 4,731,070, discloses an "Adult Incontinent Absorbent Article" which is similar to a diaper and is held in place with a belt.

Hermansson, U.S. Pat. No. 4,828,555, discloses a device similar to that of Koci, but apparently without means to hold it in place.

Dahlgren, U.S. Pat. No. 4,901,375, discloses a "Male Urinal Appliance" which includes a pouch secured to the user's body with a belt, the pouch holding a removable plastic urinal bottle.

The devices described above are either too bulky, too difficult to use, or too messy to be convenient.

SUMMARY OF THE INVENTION

The present invention provides simple, effective apparatus to help incontinent males which is easy and clean to use. The apparatus of the present invention helps incontinent men by absorbing urine which leaks from their bladders, allowing them to lead a normal daily routine with confidence that their clothing will not be wet by leaking urine. It allows comfort and freedom of movement, eliminating the need for plastic bags, diapers, and external condoms.

The present invention comprises apparatus for incontinent males including an athletic supporter having a pocket and a disposable insert to be placed in the pocket of the athletic supporter. The insert comprises a substantially cylindrical layer of absorbent material having a first, open end, and a second, closed end, an interior, and an exterior, and a waterproof material on the exterior of the layer of absorbent material. The insert is sized to receive a human penis and to be received in the pocket of the athletic supporter.

The athletic supporter may advantageously be similar to commercially available athletic supporters (jock straps), but with a pocket in which the disposable insert can be received. The disposable insert can further comprise means for making the portion adjacent the first, open end of the insert stiffer than the remainder of the insert to prevent the top of the insert from bending.

The present invention is superior to devices such as that of DeGraff because in the present invention the disposable insert, which can be placed inside an athletic supporter, can be removed after use and discarded, and the insert does not contaminate the athletic supporter, due to the insert being waterproof on the outside. In DeGraff, the insert shown in FIG. 4 wets the bag 12, thus requiring the bag 12 to be cleaned each time the insert is replaced. The present invention is superior to devices such as shown in Smith and Runeman because the athletic supporter of the present invention helps to keep the insert of the present invention firmly in place and without discomfort to the user, helping to ensure that the penis of the user remains in the insert.

The outer, waterproof, layer is preferably made of a non-wicking material so that moisture remains inside the insert and does not wick out into the pocket of the athletic supporter, where it might then wet the clothing of the user.

The disposable insert preferably includes an inner liner which separates the user's penis from the layer of absorbent material so that moisture in the absorbent layer does not come into contact with the user's skin. The inner liner is preferably a plastic, hydrophobic perforated film layer. Preferably, the inner liner comprises the same material being used commercially by Johnson & Johnson in its product Serenity TM brand incontinence pads. That material is believed to be sodium polyacrylate (a superabsorbent powder with pulp) combined with polyethylene fibers.

Advantageously, strips of adhesive tape can be provided on the insert to tape the insert to the abdomen of the user.

Optionally, a substance can be added to the absorbent layer to turn moisture in the absorbent layer into a gel to help prevent leakage from the insert.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

PARTS LIST

Figure 1:
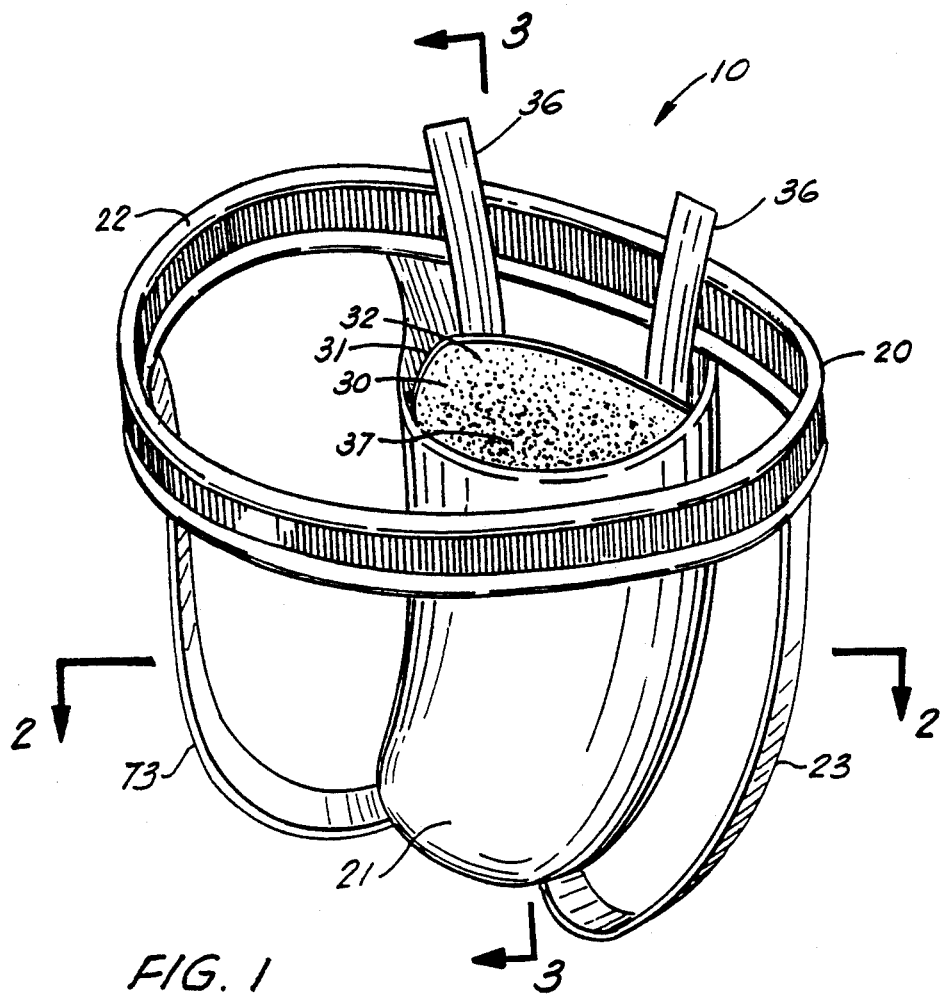
FIG. 1 is a perspective view of the preferred embodiment of the apparatus of the present invention.

The following is a list of suitable parts and materials for the various elements of the preferred embodiment of the present invention.

10: apparatus of the preferred embodiment of the present invention for assisting incontinent males
20: athletic supporter
21: insert-receiving pocket of athletic supporter 20
22: elastic waist band of athletic supporter 20
23: elastic leg bands of athletic supporter 20
30: disposable insert
31: outer, waterproof layer of disposable insert 30
32: inner, perforated film liner of disposable insert 30
33: intermediate, absorbent layer of disposable insert 30
34: stiffening cylinder in disposable insert 30
35: gel-creating substance (for example, sodium polyacrylate) in intermediate, absorbent layer 33 of disposable insert 30
36: adhesive tape strips of disposable insert 30
37: penis-receiving cavity in disposable insert 30
40: user of apparatus 10
41: penis of user 40
42: scrotum of user 40

DETAILED DESCRIPTION OF THE PREFERRED EMBODIMENT

Figure 2:
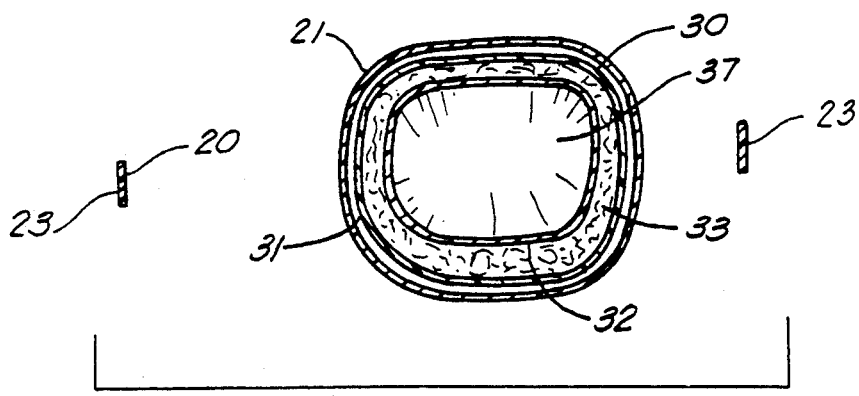
FIG. 2 is a cross-sectional view of the preferred embodiment of the apparatus of the present invention taken along the lines 2—2 in FIG. 1.
Figure 3:
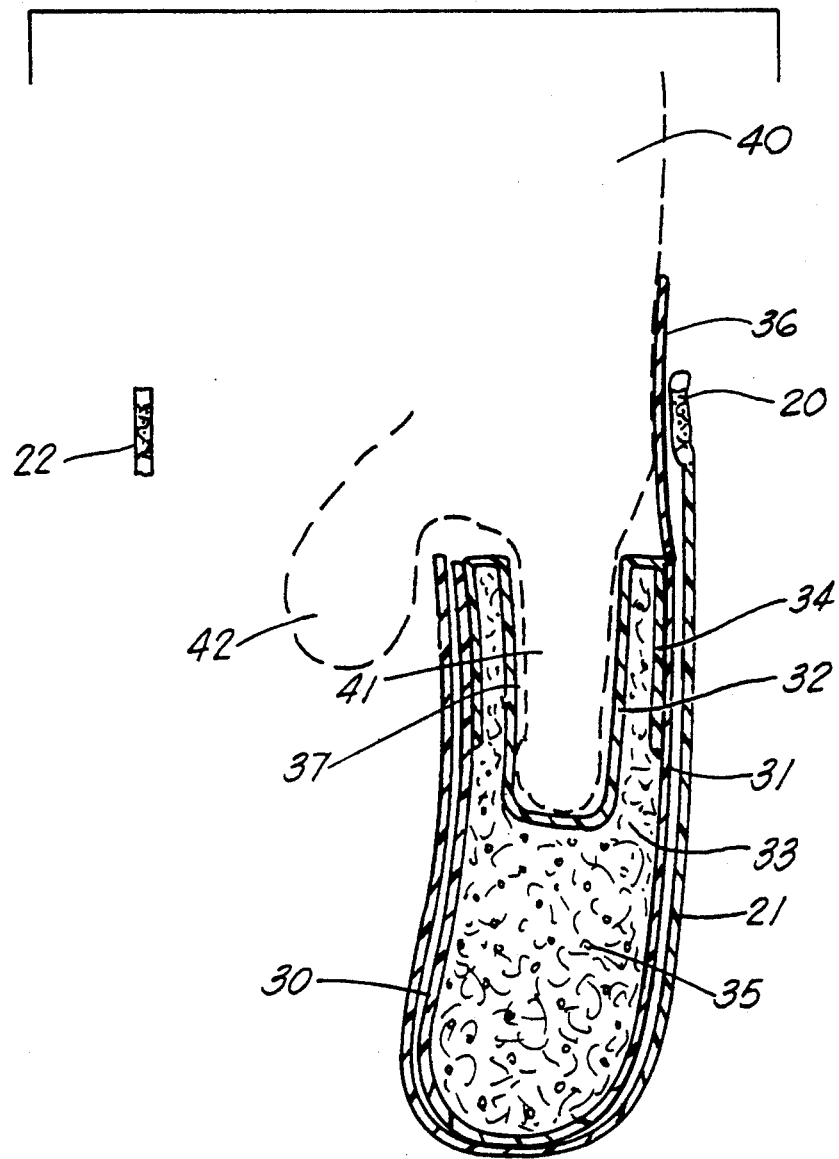
FIG. 3 is a cross-sectional view of the preferred embodiment of the apparatus of the present invention taken along the lines 3—3 in FIG. 1.

FIGS. 1 through 3 illustrate apparatus 10 of the preferred embodiment of the present invention for assisting incontinent males. Apparatus 10 comprises an athletic supporter 20 and a disposable insert 30.

Athletic supporter 20 has an insert-receiving pocket 21, an elastic waist band 22, and elastic leg bands 23. Athletic supporter 20 can be made of the same material as commercially available athletic supporters. Pocket 21 can be sewn to waist band 22 and leg bands 23 can be sewn to pocket 21 and to waist band 22.

Insert 30 includes an outer, waterproof layer 31, an inner, perforated film liner 32, and an intermediate, absorbent layer 33. Insert 30 preferably also includes an optional stiffening cylinder 34 to prevent insert 30 from bending and a gel-creating substance 35 in intermediate, absorbent layer 33 of disposable insert 30 to cause urine in layer 33 to turn to a gel to prevent it from leaking out of insert 30. Stiffening cylinder 34 made be made of plastic, for example, and may be glued to outer layer 31. Preferably, there are two adhesive tape strips 36 to secure disposable insert 30 directly to the user's abdomen to help hold insert 30 in place. Insert 30 has a penis-receiving cavity 37.

Inner liner 32 and outer layer 31 can be glued to layer 33.

Athletic supporter 20 is preferably made of a lightweight, quick-drying, stretch material and elastic. Although elastic waist band 22 is shown as being rather thin, it can be, for example, four inches wide.

Apparatus 10 is used by placing a disposable insert 30 into pocket 21 of athletic supporter 20, then placing athletic supporter 20 on the user, with elastic waist band 22 fitting around the waist of the user, the elastic leg bands 23 fitting around the legs of the user 40, and the penis 41 of the user being received in penis-receiving cavity 37 of insert 30 (see FIG. 3). Strips 36 of a special non-irritating adhesive tape serve to secure insert 30 to the abdomen of the user 40. The combination of strips 36 and athletic supporter 20 serves to hold insert 30 securely in place.

As can be seen in FIG. 3, the scrotum 42 of user 40 is not received in insert 30. Therefore, pocket 21 is preferably made of a material which will not irritate the sensitive skin of scrotum 42.

Urine which leaks from the penis 41 of the user 40 passes through inner, perforated film liner 32 of disposable insert 30 and is absorbed by intermediate, absorbent layer 33. When gel-creating substance 35 is present in layer 33, the urine turns to gel to prevent it from leaking out of insert 30. When absorbent layer 33 is saturated, or more frequently (for example, daily) if leakage from penis 41 is minimal, insert 30 is removed from pocket 21 and discarded, and a new insert 30 is inserted into pocket 21. This can be done without taking off athletic supporter 20, especially if it is to be done more frequently than daily.

As can be seen in FIG. 3, there is a relatively large amount of absorbent material (which could comprise cotton) in absorbent layer 33. Preferably between one half and three quarters of insert 30 is filled with absorbent material, with enough room being left that cavity 37 is large enough to receive the penis 41 of user 40. The more absorbent material there is in insert 30, the more urine insert 30 will be able to absorb before it needs to be replaced. The absorbent material can be, for example, the same material which is used in commercially available disposable baby diapers.

Outer layer 31 is preferably made of a non-wicking, waterproof material, such as that used on the outside of disposable baby diapers. Outer layer 31 helps prevent urine from leaking out of insert 30. Because outer layer 31 is waterproof and non-wicking, urine remains inside insert 30, and does not contaminate pocket 21. Also, insert 30, even when full of urine, can be handled without contaminating the hands of the person handling it, due to waterproof layer 31.

The apparatus of the present invention allows the wearer to have comfort, confidence, and freedom of movement which is almost impossible with other products such as diapers, external condoms, or plastic bags. Because it is disposable, the insert eliminates offending odors and the need for messy bags.

Inserts 30 of different sizes can be made for men of different sizes. Also, athletic supporter 20 could be replaced by a narrow elastic waist band and side straps to attach insert 30 to the waist band.

The foregoing embodiments are presented by way of example only; the scope of the present invention is to be limited only by the following claims.

I claim:
1. Apparatus for incontinent males comprising:
   a) an athletic supporter having a pocket; and
   b) a disposable insert to be removably placed in the pocket of the athletic supporter, the insert:
      (i) being substantially cylindrical and sized to be received in the pocket of the athletic supporter,
      (ii) having a first, open end, a second, closed end, an interior, and an exterior,
      (iii) including a layer of absorbent material,
      (iv) having a waterproof material on the exterior of the layer of absorbent material;

(v) including a cavity sized to receive a human penis;

(vi) comprising an inner liner which separates the user's penis from the layer of absorbent material so that moisture in the absorbent layer does not come into contact with the user's skin; and (vii) means, comprising a stiffening cylinder in the insert adjacent the first, open end of the insert, for making the portion of the insert adjacent the first, open end of the insert stiffer than the remainder of the insert.

2. The apparatus of claim 1, further comprising:
a strop of adhesive tape attached to the insert for securing the insert directly to the abdomen of the user of the apparatus.

3. The apparats of claim 1, wherein the inner layer comprises:
a plastic, hydrophobic perforated film layer.

4. The apparatus of claim 1, wherein:
the athletic supporter includes a waist band which fits around the waist of the user and which helps to hold the pocket adjacent the penis of the user.

5. The apparatus of claim 4, wherein:
the athletic supporter includes leg bands which fit around the legs of the user.

6. The apparatus of claim 1, further comprising:
a substance in the layer of absorbent material which combines with liquid to form a gel.

7. The apparatus of claim 1, wherein:
the layer of absorbent material includes a first portion which surrounds the cavity and a second portion which extends between the cavity and the second, closed end of the insert, the second portion having a length of between one half and three quarters of the distance between the first, open end of the insert and the second, closed end of the insert.

8. The apparatus of claim 1, wherein:
the layer of absorbent material comprises cotton.

9. Apparatus for incontinent males comprising:
a) an athletic supporter having a pocket;
b) a disposable insert to be removably placed in the pocket of the athletic supporter, an insert:
(i) being substantially cylindrical and sized to be received in the pocket of the athletic supporter,
(ii) having a first, open end, a second, closed end, an interior, and an exterior.
(iii) including a layer of absorbent material,
(iv) having a waterproof material on the exterior of the layer of absorbent material; and
(v) including a cavity sized to receive a human penis; and
(c) a strop of adhesive tape attached to the insert for securing the insert directly to the abdomen of the user of the apparatus.

10. Apparatus for incontinent males comprising:
a) an athletic supporter having a pocket and including a waist band which fits around the waist of a user of the apparatus and which helps to hold the pocket adjacent the penis of the user; and
b) a disposable insert to be removably placed in the pocket of the athletic supporter, the insert:
(i) being substantially cylindrical and sized to be received in the pocket of the athletic supporter,
(ii) having a first, open end, a second, closed end, an interior, and an exterior,
(iii) including a layer of absorbent material,
(iv) having a waterproof material on the exterior of the layer of absorbent material;
(v) including a cavity sized to receive a human penis, wherein:
the layer of absorbent material includes a first portion which surrounds the cavity and a second portion which extends between the cavity and the second, closed end of the insert, the second portion having a length of between one half and three quarters of the distance between the first, open end of the insert and the second, closed end of the insert,
the insert further comprises an inner liner which separates the user's penis from the layer of absorbent material so that moisture in the absorbent layer does not come into contact with the user's skin; and
(vi) means, comprising a stiffening cylinder in the insert adjacent the first, open end of the insert, for making the portion of the insert adjacent the first, open end of the insert stiffer than the remainder of the insert.

11. The apparatus of claim 10, further comprising:
(c) a strop of adhesive tape attached to the insert for securing the insert directly to the abdomen of the user of the apparatus.

12. The apparatus of claim 10, wherein the inner liner comprises:
a plastic, hydrophobic perforated film layer.

13. The apparatus of claim 10, wherein:
the athletic supporter includes leg bands which fit around the legs of the user.

14. The apparatus of claim 10, further comprising:
a substance in the layer of absorbent material which combines with liquid to form a gel.

15. The apparatus of claim 10, wherein:
the layer of absorbent material comprises cotton.

16. Apparatus for incontinent males comprising:
a) an athletic supporter having a pocket and including a waist band which fits around the waist of a user of the apparatus and which helps to hold the pocket adjacent the penis of the user; and
b) a disposable insert to be removably placed in the pocket of the athletic supporter, the insert:
(i) being substantially cylindrical and sized to be received in the pocket of the athletic supporter,
(ii) having a first, open end, a second, closed end, an interior, and an exterior,
(iii) including a layer of absorbent material,
(iv) having a waterproof material on the exterior of the layer of absorbent material;
(v) including a cavity sized to receive a human penis, wherein:
the layer of absorbent material includes a first portion which surrounds the cavity and a second portion which extends between the cavity and the second, closed end of the insert, the second portion having a length of between one half and three quarters of the distance between the first, open end of the insert and the second, closed end of the insert; and
(c) a strip of adhesive tape attached to the insert for securing the insert directly to the abdomen of the user of the apparatus.

17. A disposable insert to be removably placed in a pocket of an athletic supporter; the insert:
(i) being substantially cylindrical and sized to be received in the pocket of the athletic supporter,
(ii) having a first, open end, a second, closed end, an interior, and an exterior, (iii) including a layer of absorbent material,
(iv) having a waterproof material on the exterior of the layer of absorbent material,
(v) including a cavity sized to receive a human penis,
(vi) including means, comprising a stiffening cylinder in the insert adjacent the first, open end of the insert, for making the portion of the insert adjacent the first, open end stiffer than the remainder of the layer of absorbent material so that moisture in the absorbent layer does not come into contact with the user's skin.

* * * * *